(12) United States Patent
Goldbach et al.

(10) Patent No.: US 9,708,254 B2
(45) Date of Patent: Jul. 18, 2017

(54) SUPERACID FUNCTIONAL COMPOUNDS

(75) Inventors: James T. Goldbach, Avondale, PA (US); Xiaobo Wan, Qingdao (CN); David A. Mountz, Exton, PA (US)

(73) Assignee: Arkema Inc., King of Prussia, PA (US)

(*) Notice: Subject to any disclaimer, the term of this patent is extended or adjusted under 35 U.S.C. 154(b) by 0 days.

(21) Appl. No.: 13/813,510

(22) PCT Filed: Aug. 1, 2011

(86) PCT No.: PCT/US2011/046084
§ 371 (c)(1),
(2), (4) Date: Jan. 31, 2013

(87) PCT Pub. No.: WO2012/018709
PCT Pub. Date: Feb. 9, 2012

(65) Prior Publication Data
US 2013/0131201 A1    May 23, 2013

Related U.S. Application Data

(60) Provisional application No. 61/371,315, filed on Aug. 6, 2010.

(51) Int. Cl.

| | | |
|---|---|---|
| C07C 309/20 | (2006.01) | |
| C07C 323/22 | (2006.01) | |
| C07C 309/24 | (2006.01) | |
| C07C 309/81 | (2006.01) | |
| C07C 309/84 | (2006.01) | |
| C08F 12/20 | (2006.01) | |
| C08F 12/30 | (2006.01) | |
| C08F 112/14 | (2006.01) | |
| C08F 212/14 | (2006.01) | |
| C08F 12/24 | (2006.01) | |
| C08F 216/36 | (2006.01) | |
| C07F 9/38 | (2006.01) | |

(52) U.S. Cl.
CPC .......... *C07C 323/22* (2013.01); *C07C 309/20* (2013.01); *C07C 309/24* (2013.01); *C07C 309/81* (2013.01); *C07C 309/84* (2013.01); *C07F 9/3808* (2013.01); *C08F 12/20* (2013.01); *C08F 12/24* (2013.01); *C08F 12/30* (2013.01); *C08F 112/14* (2013.01); *C08F 212/14* (2013.01); *C08F 216/36* (2013.01); *C07C 2603/18* (2017.05)

(58) Field of Classification Search
USPC .............................. 525/200; 521/27; 526/243
See application file for complete search history.

(56) References Cited

U.S. PATENT DOCUMENTS

| | | | | |
|---|---|---|---|---|
| 5,795,668 | A * | 8/1998 | Banerjee | 429/492 |
| 6,933,068 | B2 * | 8/2005 | Asano et al. | 429/493 |
| 7,396,880 | B2 * | 7/2008 | Goldbach et al. | 525/199 |
| 7,449,111 | B2 | 11/2008 | Hedhli et al. | |
| 7,700,524 | B2 * | 4/2010 | Holmes et al. | 506/42 |
| 7,863,891 | B2 | 1/2011 | Kawaura et al. | |
| 2005/0077233 | A1 * | 4/2005 | Hedhli et al. | 210/500.27 |
| 2010/0197816 | A1 * | 8/2010 | Goldbach et al. | 521/27 |
| 2013/0078579 | A1 * | 3/2013 | Asano | 430/325 |

FOREIGN PATENT DOCUMENTS

| | | | |
|---|---|---|---|
| JP | 2010-204646 | * | 9/2010 |
| JP | 2010-215608 | * | 9/2010 |
| WO | WO 2010/135167 A1 | | 1/2010 |
| WO | WO-2010/135167 A1 | * | 11/2010 |

OTHER PUBLICATIONS

Kang et al., "Farnesyl-Derived Inhibitors of Ras Farnesyl Transferase", Biochemical and Biophysical Research Communications, vol. 217 (1), pp. 245-249 (1995).*

* cited by examiner

*Primary Examiner* — Mark Kaucher
*Assistant Examiner* — Henry Hu
(74) *Attorney, Agent, or Firm* — Thomas F. Roland

(57) ABSTRACT

The invention relates to a novel synthesis method for forming superacid functional molecules that include monomers, as well as new polymers and copolymers formed from the monomers, and uses for these superacid molecules, polymers, and copolymers. The superacid molecules have an alpha, alpha-difluorosulfonic acid functionality that can be obtained by a reaction between various Grignard reagents and an alkyl(2-fluorosulfonyl)-1,1-difluoroacetate, such as methyl (2-fluorosulfonyl-1,1-difluoroacetate. The molecules, polymers and copolymers would be expected to have enhanced ion conductivity, and would be useful in a variety of applications, including as ion-conductive materials, surfactants, and ion exchange resins.

5 Claims, No Drawings

SUPERACID FUNCTIONAL COMPOUNDS

This application claims benefit, under U.S.C. §119 or §365 of PCT Application Number PCT/US2011/046084, filed Aug. 1, 2011, and U.S. Provisional Application No. 61/371,315, filed Aug. 6, 2010.

FIELD OF THE INVENTION

The invention relates to a novel synthesis method for forming superacid functional molecules that include monomers, as well as new polymers and copolymers formed from the monomers, and uses for these superacid molecules, polymers, and copolymers. The superacid molecules have an alpha,alpha-difluorosulfonic acid functionality that can be obtained by a reaction between various Grignard reagents and an alkyl(2-fluorosulfonyl)-1,1-difluoroacetate, such as methyl (2-fluorosulfonyl-1,1-difluoroacetate). The molecules, polymers and copolymers would be expected to have enhanced ion conductivity, and would be useful in a variety of applications, including as ion-conductive materials, surfactants, and ion exchange resins.

BACKGROUND OF THE INVENTION

Polyelectrolytes have been blended with poly(vinylidene fluoride) and its copolymers (KYNAR PVDF from Arkema Inc.) to take advantage of the physical, chemical, electrochemical, and transport properties characteristic of both the PVDF and the polyelectrolyte components. Films of these polymer blends are useful as fuel cell membranes, and other applications such as water purification, humidification, and as separators for batteries.

A critical limitation of the current materials is that the desirable proton conductivity performance declines rapidly as the local relative humidity decreases. This has implications for the use of these materials as fuel cell membranes and constant externally applied humidification is required for the material to remain at peak performance. This constraint adds cost and complexity to the overall system.

One means for improving the performance is described in PCT/US10/34830, incorporated herein by reference. The reference describes monomers and resultant (co)polymers containing multiple acid groups per monomer unit. It also incorporates the idea of fluorinated or perfluorinated analogues thereof. The reference further describes the synthesis and use of styrenic-type monomers bearing more than one acid group. The disulfonated styrenic monomer and copolymer, blended with PVDF was cast into membranes that showed a marked improvement in the ion-conductivity and in-cell performance under reduced relative humidity conditions.

The industry is always seeking means for obtaining a further increase the proton conductivity of the polyelectrolyte phase. Besides incorporating more acid groups, ion-conductivity may be enhanced by increasing the acidity of the functional groups on the polyelectrolyte. Surprisingly, a relatively simple and benign method has now been found to incorporate an α,α-difluorosulfonic acid functionality (superacid functionality) into the polyelectrolyte. Additionally, the new synthesis process is robust and useful with a large range of different Grignard reagents, providing a family of new superacid functional molecules, including but not limited to monomers. It is expected that polyelectrolytes bearing this functionality will have enhanced proton conductivity properties over those used in previous generations.

Further, the present invention contemplates a facile, high-yielding and generally-applicable synthetic methodology by which a myriad of compounds containing alpha,alpha'-difluorosulfonic acid functionality can be synthesized. Other methods for the introduction of this superacid functionality involve the use of highly reactive and/or toxic materials, (elemental fluorine, tetrafluoroethylene, $SO_3$, etc.), whereas this procedure is relatively benign.

The few other methodologies available for the introduction of this superacid functionality into molecules, involve multiple transformations using highly reactive and/or toxic reagents (elemental fluorine, tetrafluoroethylene, $SO_3$ gas, etc.). The most auspicious of these being the ring opening of (highly toxic) perfluorinated sultones, a chemistry that is used to synthesize the acidic monomer used in NAFION ionomer membranes, commercialized by E. I. DuPont de Nemours Co. Other processes have been described such as the oxidation of α,α'-difluorothiols or thioacetates, however these routes typically involve multiple steps, scantly available starting materials, and low yields.

The present invention is useful in many fields, including ion-conductive membranes, ion-exchange resins, flocculants, metal adhesives, surfactants, water-soluble pharmaceuticals, and other applications where a very strongly acidic, strongly anionic, and/or strongly hydrophilic material is needed.

SUMMARY OF THE INVENTION

The invention relates to a composition having the following formula:

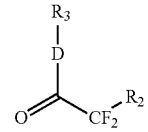

where:
D=a bond, aryl, substituted aryl, alkyl, alkeneyl, alkynyl, fluoro or perfluoro analogues thereof of $C_1$ to $C_{32}$,
$R_3$=hydrogen, vinylic, alkyl, alkeneyl, alkynyl, fluoro or perfluoro analogues thereof of $C_1$ to $C_{32}$,
$R_2$=a group selected from the group consisting of sulfonate, sulfinate, sulfonyl halide, phosphonate, phosphinate, and carboxylate, and has a counterion, $M^+$, associated with it which is an alkali, alkaline earth, transition metal cation, or organic counterion.

The invention further relates to a composition having the formula:

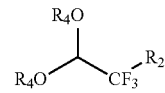

where:
$R_4$ alkyl, alkeneyl, alkynyl, aryl, fluoro or perfluoro analogues thereof of $C_1$ to $C_{32}$,
$R_2$=a group selected from the group consisting of sulfonate, sulfinate, sulfonyl halide, phosphonate, phosphinate, and carboxylate, and has a counterion, $M^+$, associated with it which is an alkali, alkaline earth, transition metal cation, or organic counterion.

The invention also relates to a homopolymer or copolymer composition having the formula:

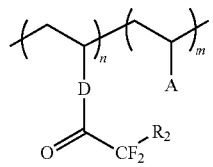

where:
D=a bond, aryl, substituted aryl, alkyl, alkeneyl, alkynyl, fluoro or perfluoro analogues thereof of $C_1$ to $C_{32}$
$R_2$=a group selected from the group consisting of sulfonate, sulfinate, sulfonyl halide, phosphonate, phosphinate, and carboxylate, and has a counterion, $M^+$, associated with it which is an alkali, alkaline earth, transition metal cation, or organic counterion.
A=a group capable of promoting cross-linking including alkene, alkylketone, aryl, alkyl or aryl ester, alkyl or aryl amide, hydroxyl, amine, epoxide, aldehyde, isocyanate, carboxylic acid, fluoro or perfluoro, or multifunctional analogues thereof,
m=0 to 19,998,
n=2 to 20,000,
the ratio of n to m=from 1 to 99%, and the value of n+m=2 to 20,000

Further, the invention relates to a process for forming a super acid, as illustrated below,

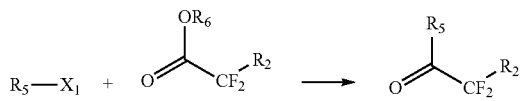

including the step of reacting an organometallic component (1) with a reagent bearing at least one functional group chosen from: sulfonyl halide, sulfonic acid, sulfonate salt, and at least one functional group chosen from: carboxylic acid, carboxylate ester, carboxylic salt (2); to produce as the primary product a compound (3) bearing an organic fragment from reagent (1), a ketone functionality, an organic fragment from reagent (2), and at least one functional group chosen from: sulfonyl halide, sulfonic acid, or sulfonate salt;
where:
$R_5$=a proton, an alkali metal cation, and alkali earth metal cation, a transition metal cation, and organic cation or an aliphatic, aromatic-aliphatic, or alicyclic hydrocarbon radical, alkenyl, alkynyl or aryl group (or fluoro or perfluoro analogue thereof) of $C_1$ to $C_{32}$.
$R_6$=$R_5$ or a different aliphatic, aromatic-aliphatic, or alicyclic hydrocarbon radical, alkenyl, alkynyl or aryl group (or fluoro or perfluoro analogue thereof) of $C_1$ to $C_{32}$.
$X_1$=alkaline earth or transition metal, alone or bound or coordinated to a halide (F, Cl, Br, I) or other appropriate counterion,
$R_2$=a group selected from the group consisting of sulfonate, sulfinate, sulfonyl halide, phosphonate, phosphinate, and carboxylate, and has a counterion, $M^+$, associated with it which is a proton, alkali, alkaline earth, transition metal cation, or organic counterion.
Another aspect of the invention is the reaction process, as illustrated below,

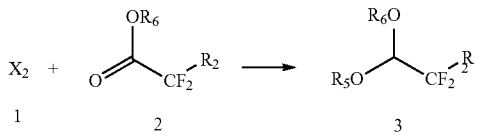

involving reacting an organometallic, or inorganic or organic reducing agent component (1) with a reagent bearing at least one functional group chosen from: sulfonyl halide, sulfonic acid, and sulfonate salt, and at least one functional group chosen from: carboxylic acid, carboxylate ester, and carboxylic salt (2), to form as the primary product a compound (3) bearing an acetal functionality, a difluoromethyl fragment from reagent (2), and at least one functional group chosen from; sulfonyl halide, sulfonic acid, or sulfonate salt.
where:
$R_5$=a proton, an alkali metal cation, and alkali earth metal cation, a transition metal cation, and organic cation or an aliphatic, aromatic-aliphatic, or alicyclic hydrocarbon radical, alkenyl, alkynyl or aryl group (or fluoro or perfluoro analogue thereof) of $C_1$ to $C_{32}$,
$R_2$=a group chosen from sulfonate, sulfinate, sulfonyl halide, phosphonate, phosphinate,
or carboxylate, and has a counterion, $M^+$, associated with it which is an alkali, alkaline earth, transition metal cation, or organic counterion,
$R_6$=$R_5$ or a proton, an alkali metal cation, and alkali earth metal cation, a transition metal cation, and organic cation or an aliphatic, aromatic-aliphatic, or alicyclic hydrocarbon radical, alkenyl, alkynyl or aryl group (or fluoro or perfluoro analogue thereof) of $C_1$ to $C_{32}$,
$X_2$=an inorganic or organic reducing agent.
The invention also relates to polymer blends having from 5 to 95 weight percent of the homopolymer or copolymer of the invention, as described above, with from 5 to 95 weight percent of a matrix polymer. The invention also relates to articles formed from these polymer blends, including articles such as a film, membrane, fuel cell, humidification device, electrolyzer, water purification device, battery, or ion exchange resin.
Further, the invention also contemplates the use of the superacid molecule of the invention for uses such as, but not limited to, surfactants, and adhesive or metal bonding agents.

DETAILED DESCRIPTION OF THE INVENTION

The invention relates to a process for synthesizing monomers having an α,α-difluorosulfonic acid (super acid) functionality, polymers and copolymers containing the superacid functionality, and end-use applications for these polymers.
The presence of fluorine in a position alpha to the sulfonic acid serves to increase the acidity of the acid by inductively withdrawing electron density around the acidic proton. The α,α-difluorosulfonic acid group is approximately 100 times stronger than its hydrogenated counterpart making it extremely interesting, as it can dramatically change the ionic nature of any molecule it is attached to. With this increased acidity, proton mobility increases under dry (or low RH) conditions, enhancing the overall proton conductivity performance of the material.

Synthesis

A general process by which α,α-difluorosulfonic acid functionality can be introduced into different molecular structures, including but not limited to polymerizable molecules is illustrated below in (Scheme 1), Scheme 1. General reaction scheme for the invention.

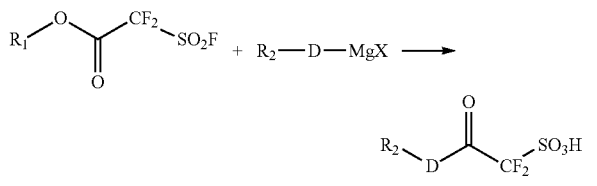

$R_1$=alkyl, aryl, cycloalkyl, heteroaryl, fluoro or perfluoro analogues thereof.

$R_2$=alkyl, alkeneyl, alkynyl, fluoro or perfluoro analogues thereof of $C_1$ to $C_{32}$.

X=Cl, Br, I

D=a bond, aryl, substituted aryl, alkyl, alkeneyl, alkynyl, fluoro or perfluoro analogues thereof of $C_1$ to $C_{32}$.

The sulfonic acid functionality in the reaction, which is the preferred acid functionality, could more generally be a group chosen from sulfonate, sulfinate, sulfonyl halide, phosphonate, phosphinate, or carboxylate, and has a counterion, $M^+$, associated with it, which is hydrogen, an alkali, alkaline earth, transition metal cation, or organic counterion.

This general reaction will be illustrated by some more specific reactions schemes. One of skill in the art can conceive of many other similar reactions with other known starting materials, based on the information and examples provided.

Difluorosulfonate-Containing Vinyl Ketones

For PVDF/polyelectrolyte blends, it is desirable to synthesize or obtain a polyelectrolyte bearing the highest mass or volume density of acid groups possible. A process to produce a polymerizable molecule bearing α,α-difluorosulfonate functionality with as small of a quantity of other groups possible was designed. Production of a vinyl ketone molecule fulfills the requirements of obtaining a readily polymerizable molecule bearing α,α-difluorosulfonate functionality as shown in Scheme 2.

Scheme 2. Overview schematic of process to synthesize 1-butene-3-oxo-4,4'-difluorosulfonate (BODFSA), an α,α-difluorosulfonate vinyl ketone monomer.

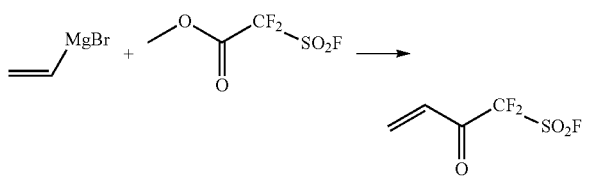

Difluorosulfonate-Containing Styrenics

Adaptation of the general process is possible using a styryl organometallic reagent, for example 4-vinylphenyl magnesium bromide as shown in Scheme 3. By this process, a styrenic-type monomer can be synthesized to fulfill the basic requirements set forth previously. While not being bond by any theory, it is believed that the styrenic monomer may be more thermally stable, more easily purified and/or polymerized since the highly electron-withdrawing $CF_2$ group is separated from the vinylic functionality by an aryl ring, providing some level of electronic and steric separation from the polymerizable center.

Scheme 3. Overview schematic of process to synthesize DFOVESA, an α,α-difluorosulfonate styrenic monomer.

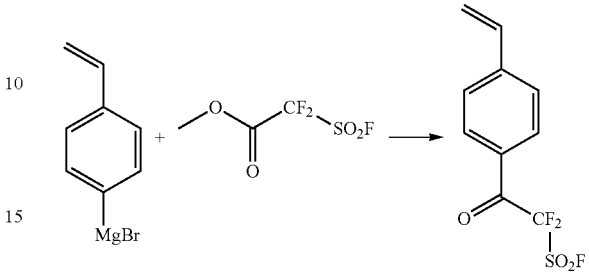

Difluorosulfonate-Containing Surfactants

Surfactants are molecules that contain both hydrophobic and hydrophilic functionalities, loosely known as amphiphilic materials. The surfactants are considered as anionic, containing a covalently-bound anionic ionizable group (sulfonate, carboxylate, phosphonic, phosphoric, borate, boric, or the like), cationic, containing a covalently-bound cationic ionizable group (ammonium, alkylammonium, alkylphosphonium, alkylsulfonium, alkylpyridinium), or non-ionic having no ionic character, the hydrophilic functionality may include ethylene oxide or propylene oxide oligomer, hydroxyl, amine, amide or other non-ionic hydrophilic functionality.

The hydrophobic functionality bound to the surfactant molecule typically is one or more long-chain ($C_8$ to $C_{20}$) aliphatics or aryl groups (phenylene, benzyl, nathphyl, anthryl, fluoreneyl, etc).

A particularly useful class of surfactants are those bearing fluorinated or perfluorinated alkyl chains. These materials combine two extremes of hydrophobicity with hydrophilicity, making them useful in dispersing highly hydrophobic materials in water such as in the example of the production of fluoropolymers under aqueous conditions. Recently, these materials have come under scrutiny as they have been found to be highly bio-persistent.

The present invention provides a synthetic process by which a non-bio-persistent, fluorinated surfactant may be produced. Molecules bearing ketone functionality are known to degrade under UV irradiation and may be susceptible to attack and degradation by microorganisms. A high-yield route to a new class of fluorinated surfactants bearing ketone and α,α-difluorosulfonate functionality is shown in Scheme 4. These surfactants would be expected to have similar physical properties to their non-ketone-containing analogues, and be non-bio-persistent.

Scheme 4. General schematic of synthesis of ketone-containing, fluorinated surfactants.

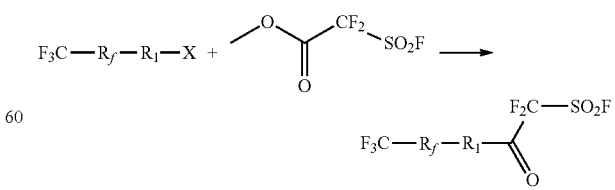

Where: $R_f$ = fluorinated or perfluorinated alkyl or aryl group of $C_0$ to $C_{24}$,
$R_1$ = non-fluorinated alkyl or aryl group of $C_0$ to $C_{10}$, X = organometallic group such as MgBr, ZnBr, CdCl, or the like.

Schemes 1-4 depict the use of methyl (2-fluorosulfonyl) difluoroacetate) as the reagent from which the α,α-difluorosulfonate radical is derived for the desired products. Schemes 2-4 depict products where the sulfonate group remains in the sulfonyl fluoride-form as in (1), however, it is conceivable that during workup procedures or purposefully in another reaction step, the sulfonyl fluoride functionality may further react. It is possible (and likely) that the sulfonyl fluoride functionality reacts with water and/or aqueous base to form a neutralized α,α-difluorosulfonic acid functionality. The counterion present associated with the α,α-difluorosulfonate functionality will depend on the type of base used, but will typically be an alkali or alkaline earth metal, or organic cation such as ammonium, alkylammonium, phosphonium, alkylphosphonium, sulfonium, pyridinium or the like.

The nature, structure, and ionic charge of the cation can have a great impact on the water or solvent solubility of the α,α-difluorosulfonate-containing molecule. For example, an organic counterion such as tetraethylammonium will impart more organic nature to the molecule, while an alkali metal such as sodium will impart more hydrophilic nature. A counterion bearing a divalent or two or more monovalent charges may cause two or more of the α,α-difluorosulfonate-containing molecules to aggregate, a property that could be beneficial in solution (for purification) or in polymeric solid form, such as in an ion-exchange resin or membrane. A general schematic of this transformation from sulfonyl fluoride form to neutralize acid form is shown in Scheme 5.

Scheme 5: General depiction of reaction of a product molecule with base, forming a neutralized α,α'-difluorosulfonic acid funtionality.

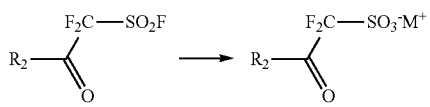

$R_2$ = alkyl, aryl, alkyl ether, fluorinated, or perfluorinated analogue thereof. $M^+$ = Mono-, di-, tri-, or tetravalent alkali, alkaline earth, transition metal or counterion.

Multiacid-Containing Molecules

The reaction process of the invention is applicable to the synthesis of molecules bearing multiple α,α'-difluorosulfonate functionalities per molecule unit. This would be expected by the use of a di-, or tri- or multi-organometallic reagent, including, but not limited to, di-magnesium halides, di-zinc halides. The reaction of such a reagent in a fashion described for mono-substituted analogues with multifunctional moieties, coupled with proper workup procedures should produce a product bearing two or more α,α'-difluorosulfonate functionalities. The molecules produced by this process could be useful in the areas of highly hydrophilic surfactants, polyelectrolytes, ionomers, membranes, dispersants, water purification chemicals, ion-exchange resins, pharmaceuticals and their intermediates.

Scheme 6. Illustration of aryl (fluorenyl) substrate conversion to include di(keto-α,α-difluorosulfonate) functionalities. Fluorenyl groups could be substituted for any di-, tri-, or multi-funtional aryl group such as ortho, meta, or para-substituted phenylene, bisphenylene, styryl, naphthyl, anthryl, peryleneyl, or heteroatom-substituted aryl such as pyridinyl, pyrimidinyl, quinolinyl, quinazolinyl, phenoxathiinyl, thianthrenyl, triazinyl, and the like.

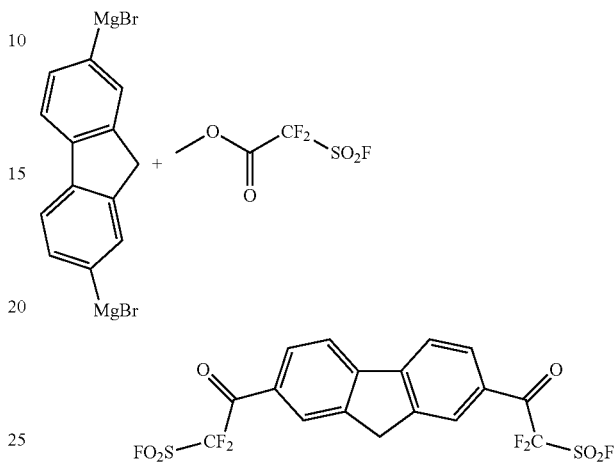

Scheme 7. Illustration of alkyl, fluoroalkyl, or perfluoroalkyl substrate conversion to include bis(keto-α,α-difluorosulfonate) functionalities.

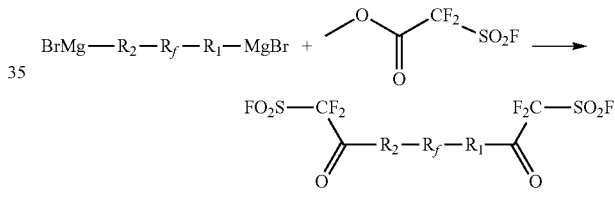

R1 and R2 = alkyl, fluoroalkyl, perfluoroalkyl, alkylene ether or cyclic analogues thereof of C0 to C10; Rf = fluoroalkyl, perfluoroalkyl, alkylene ether or cyclic analogues thereof of $C_{0-10}$.

Dihydrophilic Molecules

In addition to the production of molecules bearing single or multiple α,α'-difluorosulfonate functionality, other groups may also be present, such as acidic, basic or hydrophilic groups, that may be covalently or otherwise attached to the same molecule. These types of materials are known in the art, including isethionic acid, sulfonoacetic acid, sulfonophosphonic acid, and Zwitterions. While there are many examples of these non-fluorinated, dihydrophilic moieties, very few examples exist wherein an α,α-difluorosulfonic acid is present, due to the lack of synthetic feasibility of introduction of said group into a substrate molecule. Schemes 8, 9 and 10 illustrate routes by which these materials could be made, utilizing a variation on the synthesis method of the present invention. The introduction of the strongly-acidic α,α'-difluorosulfonate group could dramatically affect the solubility and chelating ability of such dihydrophilic materials, leading to applications in ionomers, membranes, ion-exchange resins, water purification, filtration, and the like.

Scheme 8. Prophetic example of the synthesis of phosphonated/α,α'-difluorosulfonated molecule.

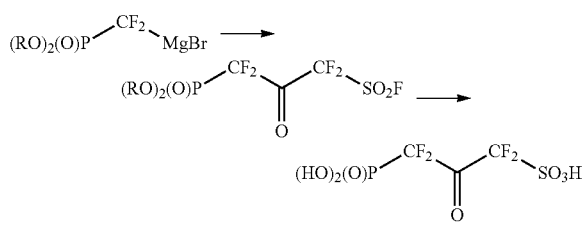

Scheme 9. Prophetic example of the synthesis of aryl-type phosphonated/α,α'-difluorosulfonated molecule.

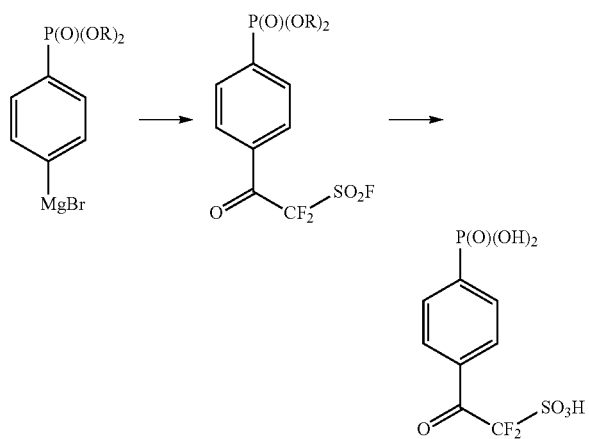

Scheme 10. Prophetic example of the synthesis of aryl-type carboxylated/α,α'-difluorosulfonated molecule. Obvious extensions include: ortho or meta-substitution, more than 2 acid/ionic functionalities, polymers/polyelectrolytes.

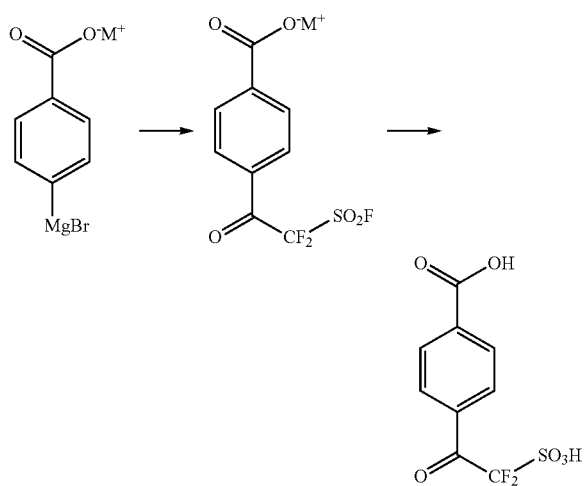

Grignard Reagents

Grignard reagents have been known since the early 1900s and are ubiquitous in organic synthesis. Practically any organic halide, particularly chlorides, bromides, and iodides, can be readily transformed into an organomagnesium reagent ("Grignard reagent") by reaction with magnesium metal under inert atmosphere. This allows for a wide array of functional and/or inert groups to be considered for this type of transformation. The Grignard reagent is known to add in a nucleophilic fashion to many substrates as well, in particular, to ketones, aldehydes, amides and esters through nucleophilic attack of the carbonyl group. Also, addition of Grignard reagents to functional groups bearing a 'good.' leaving group is possible including acyl halides, tosylates, mesylates, sulfonyl halides and the like. These two generalities provide for a wide array of synthons and resultant products that can be envisioned as useful in the present invention. Preferably, the substrate that the Grignard reagent is adding to bears an ester functionality in a position alpha-to the difluorosulfonate, allowing for the incorporation of the desired α,α'-difluorosulfonate functionality in the product.

It is contemplated that other, nucleophilic-type organometallic reagents could be used in a similar fashion. Typical examples of these types of reagents include: organo-alkali-metallics (alkyllithium, alkylsodium, and alkylpotassium), Barbier-type reagents (organo-aluminium, zinc, indium, tin or corresponding salts), Nozaki-Hiyama-Kishi reagents (organo-chromium adducts), and the like. Non-carbon-centered nucleophiles may be useful in this type of transformation, such as hydroxide, cyanide, amide, thiolate, thiocyanide, phosphine, azide, halide, or the like.

It was found, in the case of aryl Grignard (magnesium halide organometallics) that magnesium bromide adducts were much more efficient at performing the desired transformation (higher yield, better purity) than analogous magnesium chlorides.

As part of the trade-off in using a more reactive organometallic reagent (MgBr vs. MgCl) it was found that reducing the reaction temperature to −80° C. resulted in higher yield and purity. This is likely a fundamental trade-off in the system, as a higher temperature may be used if a less-reactive organometallic were used.

Reaction with Non-Organometallic (Inorganic or Organic) Reducing Agent(s)

As an extension of the present invention, the reaction of methyl (2-fluorosulfonyl)difluoroacetate with relatively mild inorganic reducing agents was tested. Surprisingly, it was found that methyl (2-fluorosulfonyl)difluoroacetate could be transformed nearly quantitatively into 1,1'-difluoromethylsulfonato-1,1'-dimethylacetal by reaction with sodium borohydride under various conditions. This was very unexpected, as the usual action of sodium borohydride on ester-containing molecules is direct reduction of the ester functionality to alcohol, not formation of an acetal as was observed. The nature of the product was unambiguously determined using $^1$H, $^{13}$C, $^{19}$F, and $^1$H/$^{13}$C 2D-NMR techniques. While not being bound by any particular theory, it is believed the reaction mechanism pathway to form the observed product is as depicted in Scheme 11. Based on this reaction pathway, obvious extensions include the use of various alcohols to change the nature of the alkyl or aryl groups attached to the acetal oxygens. These groups could conceivably contain other functionalities as well including fluoro or perfluorinated, polymerizable, biologically-active or other groups of interest. In addition, a wide range of inorganic reducing agents are known in the art, including diisobutylaluminum hydride, other metal borohydrides, lithium aluminum hydride, sodium amalgam, zinc/mercury amalgam, hydrogen gas coupled with metal catalyst, alkyl stannanes, alkyl silanes, nickel, zinc, borane, diborane, decaborane and the like. Any or all of these types of reducing Scheme 11. Proposed reaction pathway for formation of acetal product by reaction of methyl (2-fluorosulfonyl)difluoroacetate with sodium borohydride in methanol.

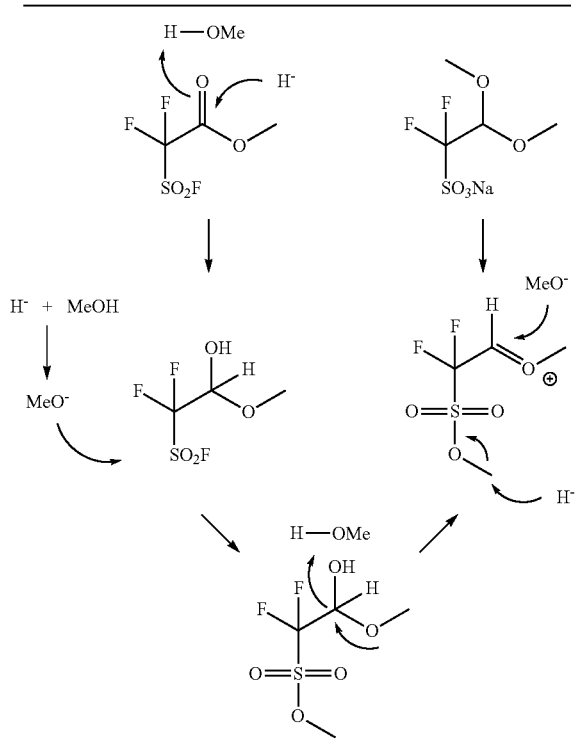

Further it is contemplated that an organic-type reducing agent be used in a similar fashion. These types of reagents include: alcohol dehydeogenase (ADH), diethyl 1,4-dihydro-2,6-dimethyl-3,5-pridinedicarboxylate (Hantzsch ester), hydrazines, hydrazides, alkyl/aryl phosphines and the like.

Polyelectrolyte Polymers and Copolymers

The superacid monomers of the invention can be homopolymerized, or copolymerized with one or more other monomers to form a copolymer. The terms polymer and (co)polymer, as used herein refer to polymers formed from one or more monomers. This includes homopolymers, copolymers, terpolymers and polymers formed from four or more monomers. Copolymer refers to both random and block copolymers, as well as graft copolymers. Copolymer is also used to describe a polymer resembling a copolymer which is formed by the partial reaction/substitution of some of the side groups of a homopolymer, resulting in a polymer backbone having two or more different moieties as side chains. The polymers of the invention contain between 2 and 20,000 monomer units.

The copolymer of the invention contains from 1 to 99 mole percent and preferably from 30 to 99 mole percent of the superacid monomer units. The remainder of the copolymer is composed of one or more ethylenically unsaturated monomers polymerizable with the superacid monomer(s).

In one preferred embodiment, at least one comonomer is a non-acid containing monomer having an aryl group (monomer B).

In order to facilitate cross-linking of the copolymer following formation into a final article of a polymer blend with a matrix polymer, at least one comonomer should contain a functionality making it capable of crosslinking. The copolymer will contain from 1-50 mole percent, preferably from 3 to 35 mole percent, and most preferably from 10 to 30 mole percent of monomers having a group capable of crosslinking. Preferably this is an aryl monomer. Crosslinking is desirable, since a fuel cell membrane relying on sulfonate or phosphonate functionalities for proton conduction will operate (at least part-time) in highly humidified or liquid water environments. Therefore, the hydrophilic portion(s) of the membrane material should be immobilized so as to be not lost to the environment by dissolution and/or leaching. The formation of a significant number of cross-links serves to bind the polymer molecules together, immobilizing them, and reducing the amount of dimensional change in the overall material. The introduction of a second, typically non-sulfonated monomer into the polyelectrolyte structure can facilitate covalent cross-linking provided that it bears a functional group capable of reacting: 1) with an externally-added cross-linking agent, 2) by application of an external impetus (elevated temperature, radiation), or 3) application of both 1 and 2.

Useful functionalities providing the ability to crosslink include, but are not limited to alcohol, primary, secondary, and tertiary amines; N-methylol acrylamide; isobutoxy methacrylamide; N-methylenebisacrylamide; allyl groups, styryl groups; and glycidyl methacrylate. Examples of secondary cross-linkers include free and blocked isocyanates, melamines, epoxies, carboxylates, α,ω-dihaloalkanes, α,ω-dialdehydes, carboxylic acids, alkoxy silanes, silicones, aziridines, and carbodiimides.

The crosslinking is typically achieved by any number of methods known to those skilled in the art. The method chosen will depend on the chemical nature and structure of the polyelectrolyte as well as the functional groups available to participate in the cross-linking reaction. In general, it is desired that the cross-linking result in functional groups that fulfill the same requirement as were set for the rest of the copolyelectrolyte including, but are not limited to: hydrolytic, thermal, and free-radical-attack stability. In addition, it is of utmost importance that the cross-linking reaction not occur prematurely, ie. prior to film casting and formation. If this were to occur, film casting may not be possible and a non-homogeneous, non-uniform product may result. It is most preferred that the cross-linking reaction takes place by either the introduction (and activation) of an external agent, termed the 'cross-linking agent' or 'cross-linker', or by the application of an external stimulus such as heat, UV radiation, or electron beam. It is also possible that the cross-linking be afforded by a combination of these methods such as would occur for the addition of a UV-active sensitizer to the blend with subsequent UV irradiation of the film. The point at which the cross-linking occurs is of utmost importance. The reaction must be controllable such that a uniform film may be cast, with subsequent activation of the cross-linking. The application of the cross-linking may occur prior to or post drying of the wet film.

Blends

The invention includes polymeric resin blends containing polyelectrolyte resins blended into a polymer or copolymer matrix. Specifically, the polyelectrolyte resins are (co)polymers without hydrolyzable groups. The matrix polymer is a tough, and highly chemical-resistant (co)polymer, preferably a fluoropolymer.

The matrix polymer can be any of the polymers and copolymers described as the matrix in US2005077233, incorporated herein by reference. Preferably, the polymer matrix contains at least one fluoropolymer. The fluoropolymer can be a homopolymer or other type of polymer, and can be a mixture of fluoropolymers or a mixture of fluoropolymer with a non-fluoropolymer. Preferably, the fluoropolymer is a thermoplastic fluoropolymer and can form a polymer blend with the other components of a formulation, including other polymers present. Preferably, the fluoropolymer is a vinylidene fluoride polymer such as a poly(vinylidene fluoride) homopolymer. Other examples of fluoropolymers include, but are not limited to, a poly(alkylene) containing at least one fluorine atom, such as polyhexafluoropropylene, polytetrafluoroethylene, poly(vinyl fluoride), or combinations thereof. More preferably, the fluoropolymer is a polymeric composition containing from about 30% to about 100 weight % of vinylidene fluoride and from 0% to about 70 weight % of at least one poly(alkylene) containing at least one fluorine atom, such as, hexafluoropropylene, tetrafluoroethylene, trifluoroethylene (VF3), chlorotrifluoroethylene, and/or vinyl fluoride. Preferably, the molecular weight of the fluoropolymer which can include homopolymers, copolymers, terpolymers, oligomers, and other types of polymers is from about 80,000 MW to about 1,000,000 MW and, more preferably from about 100,000 MW to about 500,000 MW. The fluoropolymers can be prepared using the techniques described in U.S. Pat. Nos. 3,051,677; 3,178,399; 3,475,396; 3,857,827; and 5,093,427, all incorporated herein in their entirety by reference.

The polymer blend of the present invention is an intimate blend of the polyelectrolyte and matrix polymer. The amount of matrix polymer can be from about 5 to about 95 weight % and the amount of the copolyelectrolyte can be from about 95 to about 5 weight %. Preferably, the matrix is a fluoropolymer at an amount of from about 20% to about 70 weight % and the amount of the copolyelectrolyte is from about 30 to about 80 weight %.

The blending process of the matrix polymer and copolyelectrolyte preferably involves first exchanging the alkali metal counterion of the polyelectrolyte to a proton (acidification) while remaining in aqueous solution. This acidified polyelectrolyte solution is then neutralized using the proper type and amount of organic counterion hydroxide. This involves the conversion of the protogenic/acidic groups into a tetraalkylammonium (TAA)-neutralized form. This can be achieved through various processes known in the art. Preferably the ammonium salt has a molecular weight of at least 186. Examples of suitable ammonium salts include: tetramethylammonium, tetraethylammonium, tetrapropyl ammonium, tetrabutylammonium, tetrapentylammonium, tetrahexylammonium, and asymmetric type moieties such as trioctylmethylammonium.

This aqueous solution is then converted to an organic solvent solution by addition of the appropriate organic solvent that may appropriately dissolve the matrix (co)polymer of choice with concurrent evaporation of water.

Once an organic solvent solution of organic counterion-neutralized polyelectrolyte (with low water content) is obtained, it can be combined with a separate organic solvent solution of the matrix copolymer, resulting in a homogeneous solution of both polymers. This homogeneous solution can then be processed into useful articles by standard techniques such as film casting.

Membrane Formation

Casting of the blended solution can be carried out by many different procedures familiar to those skilled in the art, such as extrusion, molding, solvent casting, and latex casting. The formed film or membrane may be used as a single layer, or may be part of a multi-layer film or membrane. A preferred method is solution casting with heating. The thickness of the formed, wet film before drying is dependent on the end-use of the material, and can vary from 1.0 μm to 2.0 mm. Preferably, the formed film has a thickness of 10.0 μm to 500.0 μm and most preferably from 20.0 μm to 500.0 μm. This 'wet' film is then dried in an air-circulating oven at elevated temperature. The time and temperature for drying the film can vary widely. The temperature used is from 20° C. to 250° C., preferably from 100° C. to 220° C., and most preferably from 120° C. to 200° C. The drying time for the wet film can also vary widely. The oven residence time should be commercially applicable and sealable in that it can be from 1.0 s to 24 h, preferably from 1.0 min. to 2.0 h, and most preferably from 1.0 min, to 45.0 min.

The thickness of the final, dried film depends on the original thickness of the wet film before drying. This thickness will vary depending on the application intended for the final article. The thickness can be from 1.0 μm to 2.0 mm, preferably from 5.0 μm to 500.0 μm, most preferably from 10.0 μm to 300.0 μm. The dried film is removed from the substrate by typical methods familiar to those skilled in the art.

The domain size of the polyelectrolyte in a cast film should be preferably less than 1.0 μm, and more preferably between 1 nm to 500 nm. The domain sizes discussed herein are with respect to maximum domain sizes and/or average domain sizes. In a preferred embodiment, the domain sizes recited are the maximum domain sizes, but can be the average domain sizes.

The proton conductivity of the polymer blend of the invention is >10 mS/cm, preferably >50 in S/cm, and most preferably >10 mS/cm. Additionally, the polymer blend has a high degree of mechanical strength, a low swelling when hydrated, hydrolytic (chemical) stability, and a low level of sulfur loss (if sulfonated) in hot water, hot acid, oxidizing and/or reducing environments.

An article, such as a membrane, produced from the polymer blend of the invention can be used as-is or further treated by an acidic washing step to remove the tetraalkyl groups, concurrently reprotonating the ionizable groups present on the starting (co)polymer component.

The copolymer blends of the invention are useful in many applications, including, but are not limited to, films, membranes, fuel cells, coatings, ion exchange resins, oil recovery, biological membranes, batteries, water purification, and the like. The resultant articles can be utilized as permselective membranes for battery, fuel cell, or electrolyzer applications. In addition, the resultant articles may be applied to electrodes for the construction of a membrane-electrode-assembly, may be imbibed with various liquids, or may be introduced onto or into a reinforcing matte or porous web to increase mechanical integrity.

A polymeric ion membrane or polyelectrolyte membrane can be made from the polymer blend of the present invention. The formed film or membrane may be used as a single layer, or may be part of a multi-layer film or membrane. The polymeric ion membrane can be prepared from conventional film preparation methods, such as melt extrusion, solvent cast, latex cast, and the like. Membrane electrode assemblies can be made from the membranes of the present invention and fuel cells using this membrane electrode assembly can be prepared. In using the polymers of the present invention to form membranes, the polymer can have any equivalent weight (g of polymer per mol of acid groups) and preferably has an equivalent weight of from about 200 to about 8,000, and preferably from about 200 to about 1,500 and even more preferably from about 200 to about 1,400 g/mol.

The compositions of the present invention are especially useful in fuel cells, batteries, and the like. The design and components used in the fuel cell and batteries would be the same as in conventional fuel cells and batteries except using the compositions of the present invention in the formation of the polymeric ionic exchange membrane. The membrane can be used alone or with conventional fillers, such as silica, carbon nanotubes and the like. The fuel cell may use a liquid or gaseous fuel such as a liquid hydrocarbon like methanol or gas like hydrogen. The fuel cell of the present invention is capable of operating at a wide range of operating conditions. The fuel cell of the present invention can have a porous support layer and an ion exchange resin wherein the ion exchange resin is supported on at least one side of the porous support layer. The present invention can be useful in hydrogen, direct methanol, or other fuel cells. Preferably, the fuel cells of the present invention have low fuel crossover, high protonic conductivity under humidified and low-humidity conditions, and/or high mechanical strength. The thickness of the membrane can be conventional but is preferably from about 0.5 to about 10 mils and more preferably from about 0.5 mil to about 5 mils. Further, the membrane preferably has an equivalent weight of from about 200 to about 2500, and more preferably about 200 to about 1400. The porous support layer can be made from any conventional material such as a fluoro-containing polymer or other hydrocarbon containing polymers such as polyolefin. The porous support layer has conventional parameters with respect to pore diameter, porosity, and thickness. The fuel cells of the present invention preferably have excellent proton conductivity, chemical resistance and low gas crossover, relatively high electrical resistance, and high protonic conductivity particularly under low-humidity conditions.

EXAMPLES

Example 1: Small Molecule Syntheses 1,1-difluoro-2-oxo-2-phenylethanesulfonate (DEOPESA)

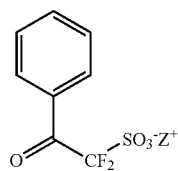

Structure of 1,1-difluoro-2-oxo-2-phenylethane sulfonate. $Z^+$=hydrogen, metal or organic counterion.

A 2-necked, 250 mL round-bottomed flask was equipped with a magnetic stir bar and 0.602 g magnesium turnings. It was purged with dry nitrogen and stirred for 18 hours. Separately, 2.63 mL of p-bromobenzene was dissolved in 20 mL of anhydrous THF in a 60 mL addition funnel. This funnel was attached to the 250 mL round-bottomed flask and 1.5 mL of the p-bromobenzene solution was added to the flask along with 50.0 μL of 1,2-dibromoethane and stirred at room temperature for 10 minutes. The remainder of the p-bromobenzene solution was then added over 1 hour and the temperature of the reaction mixture was observed to increase to reflux. External heat was applied and the mixture was refluxed for an additional 1 hour producing a clear, brown solution (the Gripard reagent). Separately, 1.26 mL of methyl 2-fluorosulfonyl-2,2-difluoroacetate (MFSDFA) was dissolved in 20 mL of THF in a single-neck round-bottom flask and cooled to −80° C., using an external acetone/dry-ice bath. The Grignard reagent solution in THF was then added to the MFSDFA solution rapidly and stirred with external cooling at −80° C. for 30 minutes. The reaction was quenched by addition of 2.0 mL of 8.0% (v/v) aqueous hydrochloric acid, then 8.0 mL of deionized water. The mixture was then allowed to gradually warm to room temperature and stirred for 18 hours.

The reaction mixture was then diluted with 10 mL of DI $H_2O$ and extracted with 50 mL of diethyl ether ($Et_2O$) with vigorous shaking in a separatory funnel. The Et2O layer was allowed to separate and was dried with sodium sulfate and filtered. The aqueous layer was then extracted four more times with 50 mL each of ethyl acetate (EtOAc). All organics were combined and solvents evaporated under reduced pressure at room temperature. $^1H$, and $^{13}C$ NMR analysis of the residue left after solvent evaporation revealed aromatic peaks indicative of the desired product $^{19}F$ NMR revealed a major peak and a very small minor peak (impurity) indicative of the desired product. Yield of crude product 3.10 g.

Example 2: 1,1-difluoro-2-oxo-2-(4-vinylphenyl) ethanesulfonate (DFOVESA)

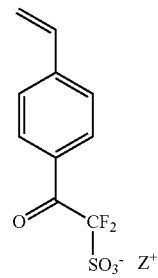

Structure of 1,1-difluoro-2-oxo-2-(4-vinylphenyl)ethane sulfonate. $Z^+$=hydrogen, metal or organic counterion.

To a 1 liter, 3-necked round bottom flask equipped with a reflux condenser, a 500 mL addition funnel and a magnetic stirrer, was charged 10.88 g of magnesium turnings (0.453 mol) and the apparatus was purged with dry nitrogen. 53.4 mL of p-bromostyrene (0.40 mol) was dissolved in 350 mL of dry tetrahydrofuran (THF) and added gradually via the addition funnel to the reaction flask with magnetic stirring to keep a gentle reflux during the addition process. The mixture was cooled to room temperature.

Methyl 2-fluorosulfonyl-2,2-difluoroacetate (33.7 mL, 0.267 mmol) was dissolved in 150 mL dry THF in a 1 liter round bottom flask and cooled to −78° C. using an external acetone/dry ice bath. The freshly prepared Grignard reagent was added dropwise to the substrate solution via an addition funnel. After finishing addition, the mixture was stirred for 1 hour at −78° C.

The reaction was then quenched with 150 mL of aqueous solution containing 11.19 g of lithium hydroxide (LiOH) (0.267 mol). The mixture was warmed gradually to room temperature. The solvent was evaporated to give a slightly yellow residue.

The residue was dissolved in 350 mL of acetone to give a yellowish suspension. The suspension was passed through a glass-sintered filter to remove the insoluble solids and the filter cake was washed thoroughly with acetone. The filtrate was evaporated at reduced pressure and room temperature to give a pale-yellow residue.

The residue was re-dissolved in 120 mL of acetone and the resulting 300 mL solution was poured into 3.0 L of dichloromethane ($CF_2Cl_2$). The solids were collected on a glass-sintered funnel and washed with $CH_2Cl_2$ and air dried.

Ethyl acetate (EtOAc, 400 mL) was added to the solid and stirred for 0.5 hour forming a solution with a small amount of insoluble precipitate. The precipitate was collected on a glass-sintered funnel and washed thoroughly with EtOAc. The filtrate was collected and the solvent was evaporated at reduced pressure. The residue was re-dissolved in acetone then a small amount of $CH_2Cl_2$ was added until the solution became cloudy. The solvent was evaporated at reduced pressure at room temperature and a white solid was obtained, which was further dried in the vacuum oven to give 34 g of product. The purity of the final product is around 92%.

Example 3: Alternative Workup Procedure

A reaction mixture was prepared as in Example 2. The reaction mixture was quenched with an aqueous solution containing 1 eq. LiOH and warmed up gradually to room temperature. An EtOAc and water was added to dilute the mixture to form two clear liquid layers. The organic layer was separated, washed with water and discarded. The aqueous layers were combined and saturated with sodium chloride (NaCl) salt, EtOAc was then used to extract the product back to the organic phase from the aqueous layer and dried with anhydrous sodium sulfate then filtered. Evaporating the solvent from the filtrate under reduced pressure gave a white solid.

Example 4: 1-butene-3-oxo-4,4'-difluorosulfonate (BODFSA)

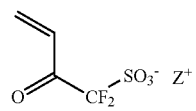

Structure of 1-butene-3-oxo-4,4'-difluorosulfonate. $Z^+$=hydrogen, metal or organic counterion.

A solution containing 40.0 mL of THF and 1.25 mL of methyl 2-fluorosulfonyl-2,2-difluoroacetate was cooled to −80° C. using an external acetone/dry-ice bath. 10.0 mL of vinylmagnesium bromide (1M solution in THF, Aldrich cat. #225584) was added dropwise with stirring and reacted for 30 min. at −80° C. after addition was complete. The reaction was quenched by adding 10 mL of 4.0 wt.-% hydrochloric acid aqueous solution. This mixture was gradually warmed to room temperature. The reaction mixture was then diluted with 30 mL of ethyl acetate (EtOAc) and 20 mL of deionized water (DI $H_2O$). The mixture was vigorously shaken in a separatory flask and allowed to separate. TLC characterization using 30% w/w EtOAc in hexanes showed UV active component in aqueous solution. $^1$H NMR analysis taken in $D_2O$ of the aqueous phase shows vinyl protons @ 6.77 ppm (dd), 6.45 ppm (d), and 5.98 ppm (d), indicative of the desired product.

Example 5: 1-butene-3-oxo-4,4'-difluorosulfonate (BODFSA)

A solution containing 20.0 mL of THF and 1.26 mL of methyl 2-fluorosulfonyl-2,2-difluoroacetate was cooled to −80° C. using an external acetone/dry-ice bath. 10.0 mL of vinylmagnesium bromide (1M solution in THF, Aldrich cat. #225584) was added dropwise with stirring and reacted for 30 min. at −80° C. after addition was complete. A 1.0 mL sample was extracted via syringe for NMR analysis. An additional 10.0 mL of vinylmagnesium bromide was then added dropwise and reacted for 30 min. at −80° C. after addition was complete. NMR analysis of the reaction mixture showed the appearance of vinylic peaks between 5.0 and 6.0 ppm, indicative of the desired product. TLC characterization of the reaction mixture showed the appearance of a non-UV-active major component indicative of the desired product.

The reaction was quenched by adding 10 mL of 8.0 wt.-% hydrochloric acid aqueous solution. This mixture was gradually warmed to room temperature. The reaction mixture was then diluted with 50 mL of diethyl ether ($Et_2O$) and 30 mL of sodium chloride aqueous solution was added. The mixture was vigorously shaken in a separatory flask and allowed to separate. 50.0 mL of 0.5M sodium bicarbonate aqueous solution was then added, and the mixture was vigorously shaken in a separatory flask and allowed to separate. TLC characterization using 30% w/w EtOAc in hexanes showed UV inactive component the organic solution indicative of the desired product.

Example 6: 1-butene-3-oxo-4,4'-difluorosulfonate (BODFSA)

A reaction procedure identical to that of Example 5 was followed, except that the MFSDFA was dissolved in 10 mL of anhydrous THF instead of 20 mL.

The reaction mixture was diluted with 5 mL of deionized $H_2O$, then extracted with 50 mL of hexane. Sodium chloride was added to the aqueous phase to saturation, then extracted four times with 50 mL each of EtOAc. All organic phases were combined and dried with sodium sulfate then filtered. The organic solvents were evaporated at room temperature under reduced pressure to give approximately 1.0 g of a brown oil. $^1$H NMR analysis of this oil revealed vinylic peaks as a major component, and $^{19}$F NMR analysis revealed a single peak, indicative of the desired product.

Example 7: 1,1'-difluoromethylsulfonato-1,1'-dimethylacetal

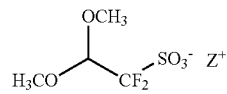

Structure of 1,1'-difluoromethylsulfonato-1,1'-dimethylacetal, $Z^+$=hydrogen, metal or organic counterion.

A 100 mL round bottom flask was equipped with 50 mL of ethanol, 1.65 mL of methyl 2-fluorosulfonyl-2,2-difluoroacetate, and a magnetic stir bar. With stirring, this solution was cooled to 0° C. using an external ice/water bath. To this solution, was added 0.98 g of sodium borohydride and 1.10 g of lithium chloride. Vigorous bubbling of the solution was observed. Stirring and external cooling was continued for 1.5 hour, at which point, 10 mL of an aqueous solution of hydrochloric acid (HCl, 1.0% w/w) was added. This aqueous solution was extracted with 25 mL of ethyl acetate using a separatory funnel. The organic phase was separated and both phases were dried in vacuo at room temperature yielding a white solid from the aqueous fraction.

Example 8: 1,1'-difluoromethylsulfonato-1,1'-dimethylacetal

A 100 mL round bottom flask was equipped with 30 mL of methanol, 1.65 mL of methyl 2-fluorosulfonyl-2,2-difluoroacetate, and a magnetic stir bar. With stirring, this solution was cooled to 0° C., using an external ice/water bath. To this solution, was added 0.49 g of sodium borohydride. Vigorous bubbling of the solution was observed. Stirring and external cooling was continued for 1.5 hour, at which point, 10 mL of an aqueous solution of ammonium chloride (saturated) was added and stirred vigorously. This aqueous solution was extracted with 25 mL of diethyl ether using a separatory funnel. TLC analysis (3:1 hexane/ethyl acetate) revealed a single product present in the aqueous phase. The organic phase contained no product.

Example 9: 1,1'-difluoromethylsulfonato-1,1'-dimethylacetal

A 100 mL round bottom flask was equipped with 30 mL of methanol, 1.65 mL of methyl 2-fluorosulfonyl-2,2-difluoroacetate, and a magnetic stir bar. With stirring, this solution was cooled to 0° C. using an external ice/water bath. To this solution, was added 0.49 g of sodium borohydride. Vigorous bubbling of the solution was observed. Stirring and external cooling was continued for 1.5 hour, at which point, 10 mL of an aqueous solution of ammonium chloride (saturated) was added and stirred vigorously. This aqueous solution was extracted with 25 mL of diethyl ether using a separatory funnel. The aqueous/methanol phase was separated and evaporated under reduced pressure yielding a white solid. $^1$H, $^{13}$C, and $^{19}$F NMR analysis of this solid (D$_2$O) confirmed that it is a mixture of 1,1'-difluoromethylsulfonato-1,1'-dimethylacetal and sodium tetramethylborate.

Example 10: 1,1'-difluoromethylsulfonato-4,1'-dimethylacetal

A 250 mL round bottom flask was equipped with 60 mL of methanol, 4.95 mL of methyl 2-fluorosulfonyl-2,2-difluoroacetate, and a magnetic stir bar. With stirring, this solution was cooled to 0° C. using an external ice/water bath. To this solution, was added 1.50 g of sodium borohydride previously dissolved in 30 mL of methanol. Vigorous bubbling of the solution was observed. Stirring and external cooling was continued for 1.5 hour. The aqueous/methanol solution was evaporated under reduced pressure yielding 7.88 g of a white solid. $^1$H, $^{13}$C, and $^{19}$F NMR analysis of this solid (D$_2$O) confirmed that it is 1,1'-difluoromethylsulfonato-1,1'-dimethylacetal (88.5% yield of theoretical).

Example 11: 1,1'-difluoromethylsulfonato-1,1'-dimethylacetal

A 2000 mL round bottom flask was equipped with 1300 mL of methanol, 96.06 mL of methyl 2-fluorosulfonyl-2,2-difluoroacetate, and a magnetic stir bar. With stirring, this solution was cooled to 0° C. using an external ice/water bath. To this solution, was added 18.92 g of sodium borohydride batchwise (5 batches of 3.78 g each). Vigorous bubbling of the solution was observed. Stirring and external cooling was continued for 1.5 hour. The aqueous/methanol solution was evaporated under reduced pressure yielding 103.50 g of a white solid. $^1$H, $^{13}$C, and $^{19}$F NMR analysis of this solid (D$_2$O) confirmed that it is 1,1'-difluoromethylsulfonato-1, 1'-dimethylacetal (90.0% yield of theoretical).

Example 12: Poly(1,1-difluoro-2-oxo-2-(4-vinylphenyl)ethanesulfonic acid)

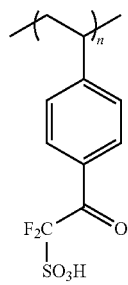

1.0 g of 1,1-difluoro-2-oxo-2-(4-vinylphenyl)ethanesulfonic acid was dissolved in 3.0 g of deionized water in a 10 ml, polymerization tube and to that solution was added 6.0 mg of Vazo56 initiator. This solution was gently sparged with dry nitrogen for 10 minutes, then heated to 65° C. for 1 hour. The solution was observed to become very viscous after 0.5 h. The solution was cooled to room temperature and added to an excess quantity of acetone to precipitate the polymer as a white powder, $^1$H NMR analysis of the powder (dissolved in D$_2$O) revealed broad peaks indicative of polymer product, poly(1,1-difluoro-2-oxo-2-(4-vinylphenyl)ethanesulfonic acid).

Example 13: Poly(1,1-difluoro-2-oxo-2-(4-vinylphenyl)ethanesulfonic acid-co-vinylbenzyl alcohol)

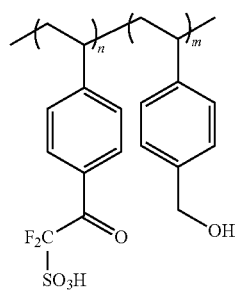

1.0 g of 1,1-difluoro-2-oxo-2-(4-vinylphenyl)ethanesulfonic acid and 0.13 g of vinylbenzyl alcohol were dissolved in 5.0 g of deionized water in a 10 mL polymerization tube and to that solution was added 10.6 mg of Vazo56 initiator. This solution was gently sparged with dry nitrogen for 10 minutes, then heated to 65° C. for 2 hour. The solution was observed to become viscous after 1.0 h. The solution was cooled to room temperature and added to an excess quantity of acetone to precipitate the polymer as a yellow-white solid. $^1$H NMR analysis of the solid (dissolved in D$_2$O) revealed broad peaks indicative of polymer product, poly(1,1-difluoro-2-oxo-2-(4-vinylphenyl)ethanesulfonic acid-co-vinylbenzyl alcohol).

Example 14: Poly(Sodium 1,1-difluoro-2-oxo-2-(4-vinylphenyl)ethanesulfonate)

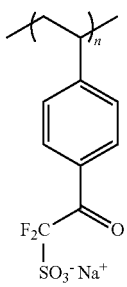

1.0 g of 1,1-difluoro-2-oxo-2-(4-vinylphenyl)ethanesulfonic acid was dissolved in 3.0 g of deionized water in a 10 mL polymerization tube. To that solution was added a solution of sodium bicarbonate in deionized water (1.0 w/w) until the pH of the solution was neutral (7.0) as estimated using pH paper (EM Science 0-14 pH range). To that solution was added 6.0 mg of Vazo 56 initiator. This solution was gently sparged with dry nitrogen for 10 minutes, then heated to 65° C.; for 1 hour. The solution was observed to become viscous after ~0.5 h. The solution was cooled to room temperature and added to an excess quantity of acetone to precipitate the polymer as a white powder. $^1$H NMR analysis of the powder (dissolved in $D_2O$) revealed broad peaks indicative of polymer product, poly(sodium 1,1-difluoro-2-oxo-2-(4-vinylphenyl)ethanesulfonate).

Example 15: Poly(Sodium 1,1-difluoro-2-oxo-2-(4-vinylphenyl)ethanesulfonate-co-vinylbenzyl alcohol)

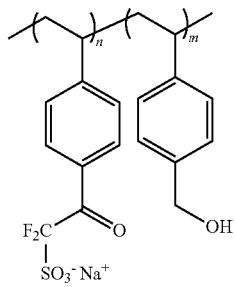

1.0 g of 1,1-difluoro-2-oxo-2-(4-vinylphenyl)ethanesulfonic acid was dissolved in 3.0 g of deionized water in a 10 mL polymerization tube. To that solution was added a solution of sodium bicarbonate in deionized water (1.0 w/w) until the pH of the solution was neutral (7.0) as estimated using pH paper (EM Science 0-14 pH range). To that solution was added 0.90 mL of 4-vinylbenzyl alcohol and 67.0 mg of Vazo56 initiator. This solution was gently sparged with dry nitrogen for 10 minutes, then heated to 65° C. for 4 hours. The solution was observed to become very viscous. The solution was cooled to room temperature and to it was added 50 mL acetone which dissolved the viscous/sticky product. This solution was transferred to a glass vial and allowed to air dry. $^1$H NMR analysis of the powder (dissolved in $D_2O$) revealed broad peaks indicative of polymer product, poly(sodium 1,1-difluoro-2-oxo-2-(4-vinylphenyl)ethanesulfonate-co-4-vinylbenzyl alcohol).

Example 16: Poly(lithium 1,1-difluoro-2-oxo-2-(4-vinylphenyl)ethanesulfonate co-vinylbenzyl alcohol)

6.524 g of lithium 1,1-difluoro-2-oxo-2-(4-vinylphenyl)ethanesulfonate was dissolved in 50.0 g of deionized water in a 100 mL round bottomed flask. To that solution was added a 0.60 mL of 4-vinylbenzyl alcohol and 1 mL of a solution of containing 48.6 mg of Vazo56 initiator previously dissolved in 10 mL of deionized water. The monomer solution was gently sparged with dry nitrogen for 15 minutes, then heated to 65° C. for 1.5 hours. The solution was observed to become very viscous. $^1$H NMR analysis of the solution (diluted with $D_2O$) revealed broad peaks indicative of polymer product, poly(lithium 1,1-difluoro-2-oxo-2-(4-vinylphenyl)ethanesulfonate-co-4-vinylbenzyl alcohol) containing 18.0 mol.-% of 4-vinylbenzyl alcohol units. Aqueous GPC analysis revealed that the molecular weight of the product was Mw-850 kDa with polydispersity index of 3.1 (relative to 10-point calibration using poly(sodium styrenesulfonate) narrow standards from 1.0 kDa to 1,000 kDa).

Example 17: Poly(1-butene-3-oxo-4,4'-difluorosulfonate) (p(BODFSA))

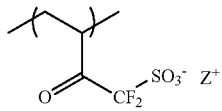

Structure of poly(1-butene-3-oxo-4,4'-difluorosulfonate). $Z^+$=hydrogen, metal or organic counterion.

1.0 g of BODFSA and 7.7 mg of Vazo56 free-radical initiator was dissolved in 10.0 ml of deionized water in a polymerization tube and sparged with dry nitrogen for 30 minutes. The mixture was heated to 65° C. for 1 hour, then 70° C. for 2 hours, then cooled to room temperature. The reaction mixture was added to an excess quantity of acetone, producing a yellow solid. $^1$H NMR analysis of this solid showed broad peaks indicative of the desired polymer product.

Example 18: Poly(lithium 1,1-difluoro-2-oxo-2-(4-vinylphenyl)ethanesulfonate-co-vinylbenzyl alcohol)

11.2235 g of lithium 1,1-difluoro-2-oxo-2-(4-vinylphenyl)ethanesulfonate was dissolved in 69 g of deionized water in a 250 mL round bottomed flask. To that solution was added a 0.8541 g of 4-vinylbenzyl alcohol and 0.0218 g of Vazo 56 free radical initiator. This solution was gently sparged with dry nitrogen for 30 minutes, then heated to 70° C. for 18 hours. The solution was observed to become viscous. Aqueous GPC analysis revealed that the molecular weight of the product was Mw=392 kDa with polydispersity index of 5.7 (relative to 10-point calibration using poly (sodium styrenesulfonate) narrow standards from 1.0 kDa to 1,000 kDa).

Example 19: Membrane Article Formed from Higher Molecular Weight Poly(1,1-difluoro-2-oxo-2-(4-vinylphenyl)ethanesulfonate-co-vinylbenzyl alcohol) and KYNAR 2801

The copolymer prepared in Example 16 was run through 89 mL of DOWEX Marathon C (Dow Chemicals, Inc.)

ion-exchange resin to remove the lithium ions and produce proton form sulfonate groups. The solids content of the acid form polyelectrolyte was 4 wt %. The acid content of the solution was determined by combining 1 g of the polyelectrolyte solution with 49 g of deionized water and titrating it to a phenolphthalein endpoint with 0.1 KOH. The acid content was $1.40 \times 10^{-4}$ mol $H^+$/g solution.

53.80 g of the acid form polyelectrolyte was combined with 3.64 g of tetrabutylammonium hydroxide solution (54.23 wt % aqueous solution supplied from Sachem Inc.) in a 200 mL flask. The pH of the ammonium-form polyelectrolyte solution was 2.4 (measured by an Acumet AR20 pH meter from Fisher Scientific). 22.1 g of ACS grade 1-methyl-2-pyrrolidone (NMP) was added to the solution. The water and some NMP in the solution were then removed using a rotary evaporator to produce a polyelectrolyte-NMP with a mass of 25.0 g.

13.60 g of the polyelectrolyte/NMP solution was combined with 9.19 g of a 21.0 wt.-% solution of KYNAR PVDF 2801 in NMP. 0.257 g of TRIXENE Bl 7982 (obtained from Baxenden Chemicals, Ltd.) and 0.0203 g of FASCAT 4202 (obtained from Arkema Inc.) were also added to this solution. The components were blended together for several hours using mechanical agitation and coated on a Mathis LTE Labdryer. The casting substrate was 2 mil thick aluminum foil with approximate dimensions of 15×12 inches. Approximately 15 g of polymer solution was spread on the foil and drawn down to a wet film thickness of about 300 microns using a doctor blade. The dry membranes were then removed from the oven and cooled to room temperature. The thickness of the dried membranes was 25-38 microns and contained a degree of opacity in some areas.

The membrane was released from the aluminum foil substrate by immersing it in a 40/60 (w/w) acetone/deionized water solution. The membrane was then exchanged to the proton form by immersing it in 3 liters of 5M aqueous sulfuric acid. The acid was heated to 80-85° C. at a rate of 40° C./hr and held in this temperature range for 1 hour. The membrane was then removed from the acid, washed with deionized water until the pH of the water was ≥4.0, and allowed to dry at room temperature.

Example 20: Membrane Article Formed from Lower Molecular Weight Poly(1,1-difluoro-2-oxo-2-(4-vinylphenyl)ethanesulfonate-co-vinylbenzyl alcohol) and KYNAR 2801

The copolymer prepared in Example 18 was run through 115 mL of DOWEX Marathon C ion-exchange resin to remove the lithium ions and produce proton form sulfonate groups. The solids content of the acid form polyelectrolyte was 3.9 wt %. The acid content of the solution was $1.40 \times 10^{-4}$ mol $H^+$/g solution.

85.0 g of the acid form polyelectrolyte was combined with 5.42 g of tetrabutylammonium hydroxide solution in a 100 mL flask. The pH of the solution after stirring was 4.37. 35 g of ACS grade 1-methyl-2-pyrrolidone (NMP) was added to the solution. The water and some NMP in the solution were then removed using a rotary evaporator to produce a polyelectrolyte-NMP with a mass of 30.5 g. Afterwards another 14.2 g of NMP was added to the solution to dissolve the ammonium-form polyelectrolyte.

6.71 g of the final polyelectrolyte/NMP solution was combined with 3.57 g of a 21.0 wt.-% solution of KYNAR PVDF 2801 in NMP. 0.13 g of TRIXENE Bl 7982 and 0.008 g of FASCAT 4202 were also added to the mixture. The components were blended, coated, and placed in an acid bath as described in Example 19. The membrane produced from this preparation had a substantially reduced amount of opacity compared to the membrane from Example 19.

What is claimed is:

1. A vinylic monomer for free-radical polymerization having the following formula:

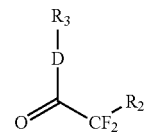

where:
D=a bond,
$R_3=R_3=C_{2\text{-}32}$ vinylic, $C_{2\text{-}32}$ alkenyl, $C_{2\text{-}32}$ alkynyl, $C_{2\text{-}32}$ aryl and fluoro or perfluoro analogues of said $C_{2\text{-}32}$ vinylic, aryl, alkenyl, or alkynyl groups, capable of forming a polymer using a free-radical initiator,
$R_2$=a group selected from the group consisting of sulfonate, sulfinate, sulfonyl halide, and carboxylate, and has a counterion, $M^+$, associated with it which is an alkali, alkaline earth, transition metal cation, or organic counterion.

2. The vinylic monomer of claim 1 having the following formula:

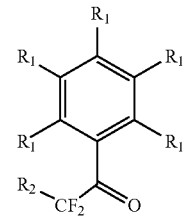

where:
$R_1$=independently is hydrogen, aliphatic, aromatic, or alicyclic hydrocarbon radical, alkenyl, alkynyl or aryl group wherein said alkenyl, alkynyl or aryl group is of $C_1$ to $C_{16}$, and the fluoro or perfluoro analogues of said $C_1$ to $C_{16}$ aryl, alkenyl or alkynyl groups, and wherein at least one of the $R_1$ groups is vinylic.

3. The vinylic monomer of claim 2 where one of the groups, $R_1$, is vinylic, and the other groups $R_1$ are hydrogen.

4. The vinylic monomer of claim 1 where $R_2$ is chosen from: sulfonyl halide, sulfonate, or sulfinate.

5. The vinylic monomer of claim 2 where one of the groups, $R_1$, is vinylic, the other groups $R_1$ are hydrogen, and $R_2$ is sulfonyl halide or sulfonate.

* * * * *

UNITED STATES PATENT AND TRADEMARK OFFICE
CERTIFICATE OF CORRECTION

PATENT NO. : 9,708,254 B2
APPLICATION NO. : 13/813510
DATED : July 18, 2017
INVENTOR(S) : James Goldbach, Xiaobo Wan and David Mountz Page 1 of 1

It is certified that error appears in the above-identified patent and that said Letters Patent is hereby corrected as shown below:

In the Specification

At Column 1, Line 7, between the Cross-Reference to Related Applications and the FIELD OF INVENTION heading, the following statement regarding federally sponsored research or development should be inserted:
--This invention was made with government support under Grant # DE-EE0000474 awarded by the Department of Energy. The government has certain rights in the invention.--

Signed and Sealed this
Eighteenth Day of November, 2025

John A. Squires
*Director of the United States Patent and Trademark Office*